United States Patent [19]

Colligan et al.

[11] Patent Number: 5,507,798
[45] Date of Patent: Apr. 16, 1996

[54] SURGICAL NEEDLE-SUTURE ATTACHMENT FOR CONTROLLED SUTURE RELEASE

[75] Inventors: Francis D. Colligan, Waterbury; Ronald H. Belcourt, Jr., Meriden, both of Conn.

[73] Assignee: United States Surgical Corporation, Norwalk, Conn.

[21] Appl. No.: 306,050

[22] Filed: Sep. 14, 1994

[51] Int. Cl.⁶ .................................................. A61B 17/00
[52] U.S. Cl. ............................ 606/224; 606/222; 606/227
[58] Field of Search ..................................... 606/222–227; 163/5

[56] References Cited

U.S. PATENT DOCUMENTS

| | | |
|---|---|---|
| 1,250,114 | 12/1917 | Bigelow et al. . |
| 1,558,037 | 10/1925 | Morton . |
| 1,665,216 | 4/1928 | Morton et al. . |
| 1,678,361 | 7/1928 | Shearon . |
| 1,757,129 | 5/1930 | McClure . |
| 1,981,651 | 11/1934 | Logan ...................................... 606/226 |
| 2,240,330 | 4/1941 | Flagg ....................................... 606/226 |
| 2,982,395 | 5/1961 | Rados . |
| 3,394,704 | 7/1968 | Dery . |
| 3,890,975 | 6/1975 | McGregor ................................ 606/227 |
| 3,910,282 | 10/1975 | Messer et al. . |
| 3,924,630 | 12/1975 | Walldorf . |
| 3,963,031 | 6/1976 | Hunter . |
| 3,980,177 | 9/1976 | McGregor . |
| 3,981,307 | 9/1976 | Borysko ................................... 606/227 |
| 4,054,144 | 10/1977 | Hoffman et al. ......................... 606/227 |
| 4,060,885 | 12/1977 | Hoffman et al. . |
| 4,072,041 | 2/1978 | Hoffman et al. . |
| 4,124,027 | 11/1978 | Boss ........................................ 606/227 |
| 4,306,443 | 12/1981 | Matsutani . |
| 4,722,384 | 2/1988 | Matsutani . |
| 4,799,311 | 1/1989 | Matsutani . |
| 4,922,904 | 5/1990 | Uetake et al. ........................... 606/226 |
| 5,046,350 | 9/1991 | Proto et al. . |
| 5,099,676 | 3/1992 | Proto et al. . |
| 5,131,131 | 7/1992 | Proto et al. . |
| 5,168,619 | 12/1992 | Proto et al. . |
| 5,230,352 | 7/1993 | Putnam et al. . |

FOREIGN PATENT DOCUMENTS

| | | | |
|---|---|---|---|
| 1121944 | 7/1968 | United Kingdom ................... 606/226 |
| 1328972 | 9/1973 | United Kingdom ................... 606/226 |

Primary Examiner—Stephen C. Pellegrino
Assistant Examiner—Jeffrey A. Schmidt

[57] ABSTRACT

A method for producing a detachable surgical needle-suture combination of the type incorporating a fluid swellable suture material is capable of producing needle-suture attachments which conform to the prescribed minimum pull-out forces for detachable needle-suture combinations as set forth in the U.S. Pharmacopeia. Generally, the method includes the steps of providing a surgical needle and a fluid swellable suture, immersing an end portion of the suture into a liquid solution whereby the suture end portion swells and assumes an expanded condition, positioning the suture end portion in its expanded condition into an aperture formed in the blunt end of the needle and swaging the blunt end of the needle to cause deformation of at least a portion of the blunt end and engagement with the suture end portion to effect needle-suture attachment.

13 Claims, 2 Drawing Sheets

STEP 1: IMMERSING THE SUTURE END PORTION INTO CONDITIONING FLUID TO EXPAND SUTURE

STEP 2: POSITIONING EXPANDED SUTURE END PORTION INTO APERTURE OF NEEDLE END

STEP 3: SWAGING THE NEEDLE END TO CAUSE DEFORMATION THEREOF TO EFFECT NEEDLE SUTURE ATTACHMENT

FIG. 2

SURGICAL NEEDLE-SUTURE ATTACHMENT FOR CONTROLLED SUTURE RELEASE

BACKGROUND

1. Technical Field

The present disclosure relates to the attachment of surgical sutures to surgical needles. In particular, the disclosure relates to a method for the attachment of surgical needles to collagenous "catgut" surgical sutures to provide a combined surgical needle-suture device possessing controlled suture release characteristics.

2. Background of Related Art

For many years, surgeons have employed needle-suture combinations in which a suture or ligature is attached to the shank end of a needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acids.

Needle-suture combinations fall into two general classes: standard needle attachment and removable or detachable needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture for various suture sizes are set forth in the United States Pharmacopeia (USP XXII 1990). The United States Pharmacopeia prescribes minimum individual pull-out forces and minimum average pull-out forces as measured for five needle-suture combinations. The minimum pull-out forces for both standard and removable needle-suture attachment set forth in the United States Pharmacopeia are hereby incorporated by reference.

One typical method for securely attaching a suture to a needle involves providing a cylindrical recess in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. Nos. 2,982,395 (adhesives) and 3,394,704 (bonding agents). Alternatively, a suture may be secured within an axial bore in a needle by swaging the needle in the region of the recess, see, e.g. U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods of detachably securing a suture to a needle are also well known. For example, a prevailing controlled release needle-suture attachment is swaged or crimped described in U.S. Pat. Nos. 3,890,975, 3,980,177, 4,060,885 and 4,072,041. In accordance with the methods taught by these patents, a suture tip is inserted into a drilled end of the needle and the needle end is swaged to engage the suture to effect needle-suture attachment.

The methods described in the above patents for forming detachable needle suture combinations are intended to provide minimum pull-out forces within a desired range. With suture materials that are stable when packaged or stored, the pull-out value remains within the targeted pull-out range. However, certain materials, such as catgut, have a tendency to expand or swell when exposed to moisture, such as conditioning fluid typically provided in the catgut suture package. As a consequence, this expansion adversely increases the pull-out force required to detach the suture from the needle.

In an effort to account for the increase in dimension of fluid swellable suture materials upon exposure to moisture and, thus, an increase in the force required to detach the suture from the needle, attempts have been made to initially decrease the swaging force during needle-suture attachment so that the pull out force subsequent to packaging (and, hence after any swelling) would be within an acceptable range. However, this approach is not feasible since the attachment force prior to packaging must be lowered to unacceptable levels. Consequently, the decreased attachment force results in the sutures having a tendency to prematurely detach during subsequent processing steps, such as packaging, thereby requiring excessive special handling.

Other attempts to accommodate for suture swelling during storage include providing a needle end having an increased dimensioned recess or axial opening to accommodate subsequent expansion of the gut suture material during storage. see, e.g., U.S. Pat. Nos. 3,924,630 and 4,124,027. However, with the methods suggested in these two patents, the suture in its dry non-swollen condition, i.e., prior to packaging in a conditioning fluid, is subject to displacement within the enlarged recess of the needle and, consequently, is prone to prematurely detach from the needle.

Accordingly, the present disclosure is directed to a method for attaching a fluid swellable suture material to a surgical needle whereby the attachment formed meets the minimum pull-out forces for detachable needle suture devices as set forth in the United States Pharmacopeia.

SUMMARY

The present disclosure is directed to a method for producing a detachable surgical needle-suture combination of the type incorporating a suture material which expands upon exposure to moisture or conditioning fluid during, for example, storage in a suture package. The method disclosed is capable of producing needle-suture attachments which conform to the prescribed minimum pull-out forces for detachable needle-suture combinations as set forth in the U.S. Pharmacopeia. Generally, the method includes the steps of providing a surgical needle and a fluid swellable suture, immersing an end portion of the suture into a liquid solution whereby the suture end portion swells and assumes an expanded condition, positioning the suture end portion in its expanded condition into an aperture formed in the blunt end of the needle and swaging the blunt end of the needle to cause deformation of at least a portion of the blunt end and engagement with the suture end portion to effect needle-suture attachment.

One of the distinct advantages of the present invention is that the suture end portion is in an expanded condition prior to the swaging attachment. Accordingly, the dimensional characteristics of the suture remain stable (since it has achieved its fully expanded condition) subsequent to the swaging operation and during storage in the suture package. Thus, the needle pullout values as controlled by the swaging operation remain substantially constant, thereby resulting in fewer rejected units.

BRIEF DESCRIPTION OF THE DRAWINGS

A preferred embodiment of the disclosure is described hereinbelow with reference to the drawings wherein:

FIG. 2 is a flow chart depicting the novel process for forming the needle-suture combination of FIG. 1.

DETAILED DESCRIPTION OF THE PREFERRED EMBODIMENT(S)

Figure 1:
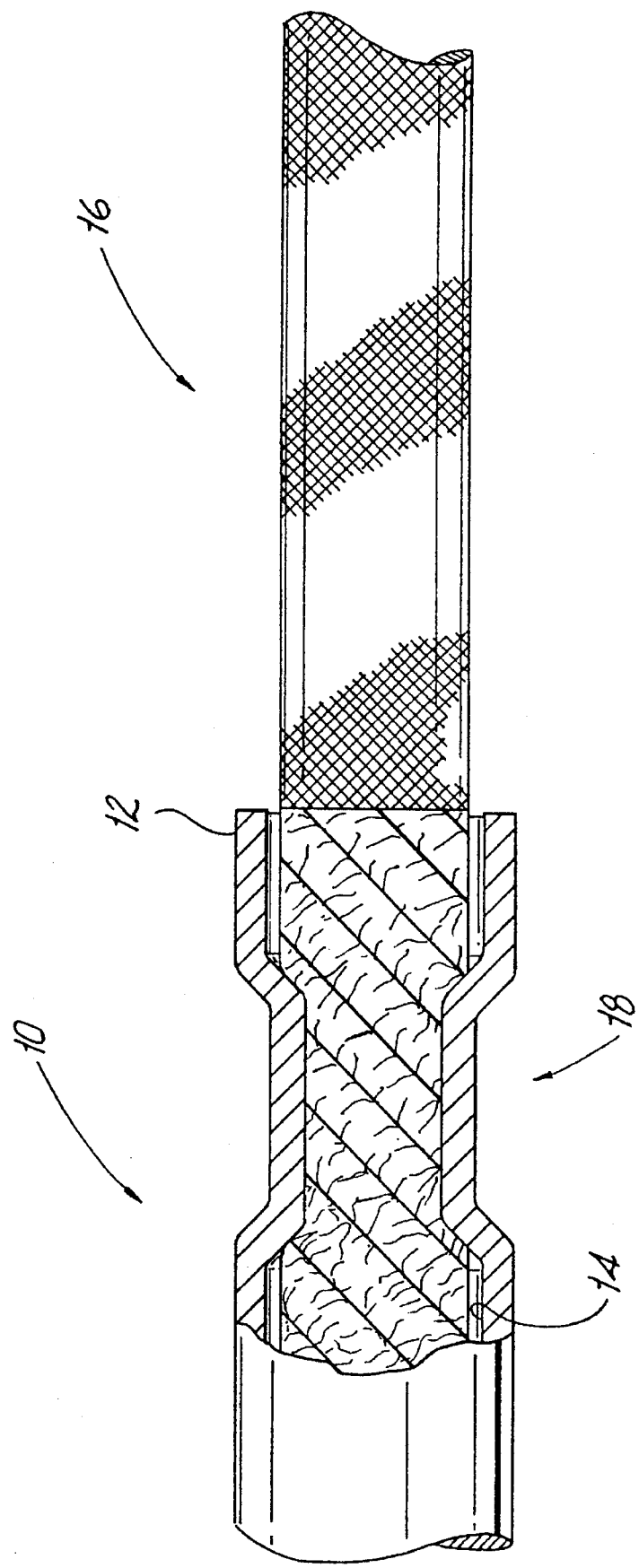
FIG. 1 is a partial cross-sectional view of a needle-suture combination in accordance with the principles of the present disclosure.

Referring now to FIG. 1, there is illustrated a surgical needle-suture combination produced in accordance with the principles of the present disclosure. Needle 10 includes drilled needle end 12 having an axial opening or bore 14 for reception of one end of suture 16. A swaged portion 18 is produced by swaging dies which causes deformation of that portion 18 whereby the inner surfaces of the needle end 12 securely engage the suture end inserted within the bore 14. Examples of suitable swaging dies for needle-suture attachment are disclosed in commonly assigned U.S. patent application Ser. No. 08/071,653, filed Jun. 2, 1993 and U.S. Pat. Nos. 5,046,350 and 5,099,676, the contents of each being incorporated herein by reference.

Needle 10 may be any type of surgical needle including curved, straight or the like, provided it has an elongated aperture or bore in needle end 12 for receiving suture 16. Preferably, the bore defines a cross sectional dimension which corresponds to the cross sectional dimension of the suture end portion in its expanded state. The needle may be fabricated from stainless steel. Suture 16 contemplated for use with the present invention is fabricated from a fluid swellable material, i.e., a material which has a tendency to expand upon exposure to moisture such as collagenous or "gut" suture material, cotton and the like.

Referring now to FIG. 2, there is illustrated a flow chart depicting the novel process for forming the needle-suture combination of FIG. 1. Generally stated, the process involves three steps. The first step involves immersing an end portion of a fluid swellable suture, e.g., gut suture material, into a liquid conditioning solution. The suture upon immersion absorbs the liquid, and consequently, expands in dimension to define a greater cross-sectioned area than in its original dry state. Thereafter, the process is continued by inserting the suture end portion in its expanded condition into the aperture or opening 14 of the drilled end 12 of the needle 10. Needle end 12 is thereafter swaged by a crimping operation to cause deformation of the needle end and contacting engagement of the inner surfaces of the needle end with the inserted suture thereby forming the needle-suture attachment.

Unlike prior art methods for attaching a fluid swellable suture to a needle, in accordance with the principles of the present disclosure, the suture is initially immersed in the conditioning fluid prior to needle-suture attachment. Thus, expansion of the suture material is complete prior to the swaging step.

Accordingly, the swaging step can be performed to produce a detachable needle-suture attachment within the desired ranges as set forth in U.S. Pharmacopeia without concern of subsequent swelling and, consequently, changes in the detachment force during, for example, storage in a suture package.

The preferred conditioning fluid utilized in the first or immersing step consists of about 89% isopropanol, 1% triethanolamine solution and 10% water. This particular mixture is commonly available and is also commonly used as a conditioning fluid in suture packages. The duration of time for immersing the gut suture may vary depending on the suture size, but, preferably extends for a minimum of twelve (12) hours before removal. This twelve hour period is sufficient to ensure complete saturation of the gut suture end such that expansion of the suture material is complete prior to insertion into the drilled end 12 of the needle 10.

The second or swaging step can be performed using any conventional swaging apparatus and die arrangement such as that disclosed in the aforementioned commonly assigned U.S. patent application Ser. No. 08/071,653 and U.S. Pat. Nos. 5,046,350 and 5,099,676. The swaging force of the dies can be readily adjusted to the parameters and dimensions of the needle and suture so as to produce a detachable needle-suture attachment. It is to be appreciated that the swaging step may alternatively be adjusted to form a non-detachable suture attachment if desired.

The suture with expanded tip portion is inserted into the needle bore and the attachment completed before the suture begins to dry out. Preferably, the suture is withdrawn from the immersion solution and promptly attached to a needle within a few hours. Most preferably, the suture is inserted into and attached to a needle within a few minutes of being withdrawn from the immersion fluid.

The present disclosure provides a needle-suture device which possesses a pull-out value within the desired range and which remains substantially stable during storage in a suture package.

While the above description contains many specifics, these specifics should not be construed as limitations on the scope of the invention, but merely as an exemplification of a preferred embodiment thereof. Those skilled in the art will envision other possible variations that are within the scope and spirit of the invention as defined by the claims appended hereto.

What is claimed is:

1. A method for producing a surgical needle-suture combination, comprising the steps of:

(a) providing a surgical needle and a suture, the needle having a blunt end with an aperture formed therein, the suture including a fluid swellable material and having an end portion suitably configured for insertion into the aperture of the needle;

(b) immersing the end portion of the suture into a liquid solution whereby the suture end portion swells and assumes an expanded condition;

(c) positioning the suture end portion into the aperture formed in the blunt end of the needle; and (d) swaging the blunt end of the needle to cause deformation of at least a portion of the blunt end such that the blunt end portion compresses the suture end portion to attach the suture to the needle.

2. The method according to claim 1 wherein step (d) involves swaging the blunt end of the needle to form a removable needle-suture attachment.

3. The method according to claim 2 wherein step (a) includes providing a suture fabricated from a collagenous material.

4. The method according to claim 3 wherein step (b) includes immersing the end portion of the suture in a solution consisting of isopropanol, triethanolamine solution and water.

5. The method according to claim 3 wherein step (b) includes immersing the end portion of the suture for a period of at least 12 hours.

6. The needle-suture combination formed in accordance with the method of claim 3.

7. The method according to claim 2 wherein step (a) includes providing a curved surgical needle.

8. The method according to claim 2 wherein step (a) includes providing a straight surgical needle.

9. The method according to claim 2 wherein step (a) includes providing a surgical needle fabricated from stainless steel.

10. The needle-suture combination formed in accordance with the method of claim 2.

11. A method for producing a surgical needle-suture combination, comprising the steps of:

(a) providing a surgical needle and a suture, the needle having a blunt end with an aperture formed therein, the suture including a fluid swellable material and having an end suitably configured for insertion into the aperture of the needle;

(b) immersing the suture end into a liquid solution whereby the suture end swells and assumes an expanded condition;

(c) positioning the swelled suture end into the aperture formed in the blunt end of the needle; and (d) swaging the blunt end of the needle to bring at least a portion of the inner surface defining the aperture into compressing engagement with at least a portion of the suture end to attach the suture to the needle.

12. The method of claim 11 wherein step (b) includes immersing the suture end in a solution consisting of isopropanol, triethanolamine solution and water.

13. The method of claim 11 wherein step (b) includes immersing the suture end for a period of at least 12 hours.

\* \* \* \* \*